United States Patent [19]

Sergunkin et al.

[11] 3,984,353

[45] Oct. 5, 1976

[54] METHOD FOR PREPARING OXYGEN COMPOUNDS OF ANTIMONY WITH METALS

[76] Inventors: Vladimir Nikolaevich Sergunkin, prospekt Osvobozhdenia Donbassa 6, kv. 41, Donetsk; Georgy Konstantinovich Boreskov, ulitsa Zolotodolinskaya, 85, Novosibirsk, Akademgorodok; Vera Alexandrovna Dzisko, ulitsa Zhemchuzhnaya, 6, kv. 3, Novosibirsk, Akademgorodok; Viktor Petrovich Karlov, prospect Vasnetsova, 3a, kv. 8, Donetsk; Vsevolod Valentinovich Klimov, ulitsa Schorsa, 45, kv. 30, Donetsk; Jury Vladimirovich Pugachev, ulitsa Khasanovskaya, 41, Donetsk; Nadezhda Mikhailovna Samokhvalova, ulitsa Bakinskikh Komissarov 14, kv. 37, Donetsk; Dzhema Vladimirovna Tarasova, ulitsa Zhemchuzhnya, 24, kv. 40, Novosibirsk, Akademgorodok, all of U.S.S.R.

[22] Filed: Feb. 25, 1974

[21] Appl. No.: 445,635

[52] U.S. Cl. ............................... 252/461; 252/462; 252/463; 252/467; 252/471; 252/472; 423/593; 423/594; 423/595; 423/598; 423/599; 423/600; 423/617

[51] Int. Cl.² .................... B01J 21/00; C01B 29/00

[58] Field of Search ............ 423/617, 87, 593, 594, 423/595, 598, 599, 600; 252/461, 472, 464, 467, 471, 475, 476

[56] References Cited

UNITED STATES PATENTS

| | | | |
|---|---|---|---|
| 3,198,751 | 8/1965 | Bethell et al. | 252/461 |
| 3,200,084 | 8/1965 | Callahan et al. | 252/456 |
| 3,338,952 | 8/1967 | Callahan et al. | 252/472 |

FOREIGN PATENTS OR APPLICATIONS

| | | | |
|---|---|---|---|
| 289,055 | 2/1971 | U.S.S.R. | 423/617 |

*Primary Examiner*—Oscar R. Vertiz
*Assistant Examiner*—Wayne A. Langel
*Attorney, Agent, or Firm*—Haseltine, Lake & Waters

[57] ABSTRACT

This invention relates to the method for preparing oxygen compounds of antimony with metals.

According to the invention, the method for preparing oxygen compounds of antimony with metals consists in oxidation of antimony trioxide by hydrogen peroxide at a temperature from 40° to 100°C to form a suspension of hydrated antimony pentoxide and interaction of the obtained suspension of hydrated antimony pentoxide with metal compounds with subsequent drying ad calcining at temperatures from 300° to 700°C.

The invention can be employed in the manufacture of metal oxide-antimony catalysts and metal-oxide resistor materials.

4 Claims, No Drawings

METHOD FOR PREPARING OXYGEN COMPOUNDS OF ANTIMONY WITH METALS

This invention relates to methods for preparing oxygen compounds of antimony with metals, and more particularly to methods for preparing oxy-compounds of pentavalent antimony with metals.

Oxygen compounds of antimony with metals belonging to groups IB, IIA, IIB, IIIA, IIIB, IVA, IVB, VA, VB, VIB, VIIB, and VIII of the Periodic Table are known to be used as catalysts in the manufacture of acrylonitrile by the reaction of oxidizing ammonolysis of propylene. Acrylonitrile is used as raw material in the manufacture of synthetic fibre, plastics, and rubbers.

Catalysts based on oxygen compounds of antimony with metals of the above named groups of the periodic system can be used for oxidation of olefines to unsaturated aldehydes and acids, for example, of acrolein and methyl acrolein into acrylic and methacrylic acids, for oxidation of olefin-ammonium mixtures into unsaturated nitriles, and also for catalytic dehydrogenation of olefins into diolefins.

Moreover, some oxy-compounds or solid solutions of antimony and tin can be used for preparing resistors.

Known in the prior art are methods for preparing oxygen compounds of antimony with metals. They are as follows.

Treating a mixture of elemental antimony and corresponding metal with nitric acid and oxidation of the mixture by oxygen, or a gas containing oxygen, with heating.

Another method consists in heating mixtures of antimony oxides and oxides or hydroxides of a metal in the presence of substances that are destroyed by heating, for example ammonium chloride, ammonium nitrate, salts of thiourea, etc.

Still another method of preparing oxygen compounds of antimony with metals is the heating under oxidizing conditions of mixtures of organic or mineral salts of antimony with organic or mineral salts of the metal.

Known also is the method for preparing oxygen compounds of antimony with metals in which antimony oxides and oxides or hydroxides of metals are pecipitated from their salts in an aqueous medium by a base, and the thus obtained mixed precipitate is heated in the presence of oxygen or a gas containing oxygen.

Furthermore, known is the method for fusing a hydrate of metal nitrate with one or several oxides of antimony, with subsequent heating of the mass in the presence of oxygen or a gas containing oxygen.

Known also is the method of hydrolysis of chlorides of antimony and the corresponding metals, with separation of hydrochloric acid, and heating the thus obtained mixed precipitate in the presence of oxygen or a gas containing oxygen.

The feature that is common to all these methods for preparing oxygen compounds of antimony with metals is the preparation of antimony pentoxide, for example by treating metallic antimony with nitric acid, or by hydrolysis of antimony pentachloride, or oxidation of antimony trioxide by nitric acid, or else by oxidation of antimony trichloride solution by hydrogen peroxide or nitric acid, etc. Next step is the interaction of the obtained antimony pentoxide with metal compounds, which is effected by mixing antimony pentoxide with the metal compounds with subsequent thermal treatment.

The method based on the oxidation of antimony compounds (metallic antimony, antimony trioxide, etc). by nitric acid with addition of metal, for example, iron nitrate, with subsequent precipitation of the obtained mixture by ammonia, filtration and washing of the precipitate, which is then slowly dried and calcined, is the most widely used method of those mentioned above.

This method is covered by U.S. Pat. Nos. 3,546,138 3,197,419; 3,200,084; 3,200,081; 3,198,750; 3,341,471; British Patents Nos. 3,244,642, 3,152,570; 3,309,325; 3,346,513, Japanese Patents Nos. 282,171; 336,856; 340,131, Belgian Patent No. 189,769 and French Patent No. 1,168,279.

Oxygen compounds of antimony and iron (U.S. Pat. Nos. 3,197,419 and 3,546,138) are prepared by oxidizing metallic antimony, antimony trioxide, antimony tetraoxide by hot concentrated nitric acid until red oxides of nitrogen stop evolving. Then an aqueous solution of iron nitrate is added and the obtained mixture is precipitated by ammonium hydroxide at pH 7.6–8.0. The thus obtained precipitate is separated by filtration, washed, and then dried at a temperature of 120° C with subsequent calcining at 800°–900° C.

In order to improve mechanical strength of the precipitated material, a 30 per cent colloidal solution of silicon dioxide, and activating additives, for example, rhenium nitrate, are added to the mixture before precipitation. The obtained material is used as a catalyst.

Oxycompounds of antimony and manganese (U.S. Pat. No. 3,200,081) are prepared by oxidizing powdered metallic antimony by hot nitric acid until nitrogen oxides stop evolving, subsequently mixing the obtained suspension with a solution of manganese nitrate, and precipitating by ammonia solution.

The obtained mixture is dried at a temperature of 120° C and calcined for 12 hours at a temperature of 425° C, and then calcined again for 12 hours at a temperature of 760° C in an open stove.

U.S. Pat. No. 3,200,084 describes a method for preparing an antimony-cerium catalyst consisting in that ground metallic antimony is oxidized by nitric acid at the temperature of its boiling point until nitrogen oxide vapour stops evolving; next cerium nitrate solution is added, the mixture is precipitated by adding a 28 per cent solution of ammonia, the precipitate is separated by filtration, washed with water while bubbling air through the precipitate during washing, with subsequent drying the precipitate at a temperature of 120° C, calcining at a temperature of 435° C and activation at a temperature of 760° C in an open stove.

Disadvantages inherent in the known methods for preparing oxygen compounds of antimony with metals are that the processes consist of many steps, and the quantities of wastes (washings, noxious gases) are large.

For example, during oxidation of metallic antimony by nitric acid, about 900 cu.m. of nitrogen oxides per ton of metallic antimony are liberated (calculated at standard temperature and pressure).

When a combined precipitate of iron hydroxide and antimony hydroxide is washed, 40 cu.m. of water are required per ton of dry material. These washings are contaminated by antimony compounds and ammonium nitrate, and hence require purification from antimony and ammonium salts, which is a labour-consuming operation too.

Moreover, when the said raw materials are used in the process, the strength of the obtained catalyst particles is low which makes it difficult to the product as fluidized-bed catalysts.

The object of this invention is to work out a method for preparing oxygen compounds of antimony with metals which would make it possible to prepare the said compounds in a process comprising only few steps, to intensify the process, and to decrease the loss of raw materials. Another object of the invention is to work out a process requiring no washing with water, and in which no noxious gases are liberated.

These objects have been attained in the proposed method for preparing oxygen compounds of antimony with metals in which antimony trioxide is oxidized into antimony pentoxide by hydrogen peroxide in quantity not less than stoichiometric in an aqueous medium at temperatures from 40° to 100° C, the obtained antimony pentoxide is reacted with a salt, a hydroxide or an oxide of at least one of the metals, the obtained product is dried at temperatures from 100° to 250° C and calcined at a temperature from 300° to 700° C.

The use of hydrogen peroxide as an oxidant in the proposed method offers certain advantages over the known methods in which nitric acid is used as the oxidant. The proposed method also obviates the step of precipitation of hydroxides of antimony and metals that are formed after oxidation and rules out their subsequent washing to neutral reaction. As a result, the complicated and expensive operations for purifying washing waters (which otherwise are required in ample quantities) from antimony and metals that are harmful for the environment, are obviated too. Moreover, noxious nitrogen oxides are not liberated into atmosphere any longer either.

The requirement for hydrogen peroxide is determined by the stoichiometry of the reaction of antimony trioxide oxidation into antimony pentoxide. Practically a small excess of hydrogen peroxide is required to oxidize antimony trioxide, which is only needed to remove the effects of such unaccountable factors as insignificant impurities contained in raw materials, the inhibiting action of the construction material of the reaction vessel, etc.

Hydrogen peroxide having the concentration from 33 to 5 per cent by weight can be used in the proposed method. The size of particles of hydrated antimony pentoxide can be adjusted by varying the quantity of water, and the intensity of the process and the degree of crystallinity of the hydrated antimony pentoxide can be controlled by the varying the process temperature.

The preferable ratio of the solid to liquid phases at the stage of antimony trioxide oxidation, and also at the step of mixing the hydrated antimony pentoxide and the metal compound is 1:4.

The preferable temperature of the process is 80° C.

The formed antimony pentoxide in the hydrate state stabilizes hydrogen peroxide, which decreases its loss in the process of oxidation, by preventing spontaneous oxidation of hydrogen peroxide.

Mixing the freshly prepared hydrated antimony pentoxide with metal compounds at a temperature from 40° to 100° C ensures the chemical interaction between the metal compounds and the hydrated antimony pentoxide directly at the mixing stage or produces solid solutions which makes it possible to decrease the temperature of calcining to increase the strength of the particles, and to adjust within wide limits the specific surface of the catalyst which is a very important factor for the catalyst.

The proposed method makes it possible to prepare oxygen compounds of antimony with the following metals and elements: Fe, Sn, Bi, Ni, Co, V, Mo, W, Cr, Ce, Mn, Ti, Al, $Sb^{III}$, cum, Ca, Ba, Mg, Pb, Nb, Ta, Te, P and B.

If a metal compound is not a catalyst in the reaction of hydrogen peroxide decoposition, then, with the purpose of decreasing the number of steps of the process, it is recommended to process antimony trioxide by hydrogen peroxide in the presence of compounds of Sn, Ti, La, Al, Mo, W.

In this version of the method the step of mixing the hydrate of antimony pentoxide with metal compounds is obviated since the formation of antimony compounds with metals proceeds simultaneously with oxidation of antimony trioxide by hydrogen peroxide (in one reaction zone).

It is recommended to utilize metal hydroxides as metal compounds in the proposed method for preparing oxygen compounds of antimony with metals. This eliminates wastes, increases the yield of the end product to 100 per cent and prevents contamination of the end product with undesirable impurities.

It is recommended to prepare oxygen compounds of antimony and iron taking iron hydroxide, as the metal compound. The weight ratio of iron hydroxide to antimony pentoxide in this case should be 1:4, calculated as the corresponding oxides ($Fe_2O_3:Sb_2O_5 = 1:4$).

Making use of the iron hydroxide completely eliminates wastes of the process, and the material obtained possesses high mechanical strength.

Oxygen compounds of antimony with iron are widely used in industry as catalysts in the processes of oxidizing ammonolysis of propylene in the manufacture of acrylonitrile. The oxygen compound of antimony with iron according to this invention contains one part by weight of $Fe_2O_3$ per four parts by weight of $Sb_2O_5$. This compound is one of the most widely used catalysts used in oxidation processes. The proposed method provides for a more readily realizable process for preparing the catalyst compared with the previous art processes.

Whenever it is necessary to modify the antimony-iron catalyst by additives of other metals componds, this can be done without increasing the number of process steps, but simply by adding the required compounds in the required quantities at the step of mixing with the iron compounds.

At the present time metal antimonates are prepared by multi-step processes, which are labour-consuming and require high temperatures (above 1300° C). According to the invention metal antimonates should be prepared by mixing antimony pentoxide hydrate with the metal compound in stoichiometric quantities.

The obtained material is dried by known techniques, preferably by spraying at temperatures from 120° to 200° C.

It is recommended to calcine the product at a temperature from 300° to 700° C. This temperature is lower that the calcining temperatures in the prior art methods, and this lowering becomes possible due to the fact that during mixing hydrated antimony pentoxide with metal compounds at temperatures from 40° to 100° C, solid solutions are formed as a result of chemical interaction between the components.

The proposed method has the following advantages.

The process flow-sheet is simplified significantly, since some of its stages, such as precipitation of antimony hydroxide and metal hydroxides by a base from said solutions, filtration and washing of the obtained precipitates, are eliminated.

The process equipment is simple, too.

Owing to the use of hydrogen peroxide as the oxidant, contamination of washings with antimony is eliminated and no noxious gases are discharged into atmosphere.

The elevated temperatures of the oxidation process significantly increase the process rate and ensure the preparation of hydrated antimony pentoxide in the crystal state and in the hydrogen ion form.

The preparation of crystalline antimony hydrate in the ionic form ensures the formation of the oxygen compound of antimony with the metal already at the stage of its mixing with the metal compound, as a result of which the calcining temperature can be decreased significantly.

The hydrated antimony pentoxide can be used as a finished product, namely as a cation exchange material in the hydrogen form, and can also be used in chemical, metallurgical and other branches of industry where ion separation is required, for example for isolation on alkali and alkaline-earth metals from solutions containing negligibly small quantities of these elements.

Since the number of process stages in decreased, and due to abolishing the washing step, the loss of materials is decreased too; hence the yield of the end product increases.

The proposed method ensures preparation of both metal antimonates and metal oxide-antimony catalysts having high mechanical strength, which makes it possible to utilize them in fluidized bed catalysis.

The measure of mechanical strength (loss in per cent by weight during 100 hours of operation at a linear velocity of air in the tube of 10 cm/sec) for the catalyst prepared by the proposed method is less than 0.3 per cent less, while this loss for the catalyst prepared by the know methods is from 1.5 to 3.4 per cent.

Below follows a description of a preferable method for realization of the proposed method.

According to the invention, oxygen compounds of antimony, for example with iron, are prepared as follows. An enamelled reaction vessel provided with a stirrer is loaded with 155 liters of desalted water and heated to 80° C. Then, with stirring, are added 83.5 kg of antimony trioxide and 90 liters of a 30 per cent hydrogen peroxide solution which corresponds to the molar ratio of 1:3, respectively. The suspension is kept for 30–60 minutes and then, with stirring, added are 32.3 kg of iron hydroxide (as $Fe_2O_3$) which corresponds to the ratio $Fe_2O_3$ to $Sb_2O_5 = 1:4$. The reaction mixture is stirred for 30–60 minutes and then spray-dried at a temperature of 200°–250° C. The dry powder is collected in cyclones from where it is delivered into a rotary kiln where it is processed at a temperature of 700° C for 30–60 minutes. The thus obtained end product has the specific area of 47.6 sq. m/g, and the mechanical strength for crushed fraction of 100–200 micron is 90 per cent (as tested in a chamber with a rotary impeller at 3500 rpm for 40 minutes).

The degree of propylene conversion with the obtained catalyst is 80.3 per cent, the selectivity for acrylonitrile is 57.9 per cent. The determination was carried out on a pass-through - circulation plant in a fluidized bed of the catalyst.

For a better understanding of the invention, the following examples of its practical embodiment are given by way of illustration.

EXAMPLE 1

A reaction vessel is loaded with 100 ml of water into which 50 g of $Sb_2O_3$ are added with stirring. The obtained suspension is heated to 40° C and 50 ml of a 30 per cent solution of hydrogen peroxide are added. The components are mixed for 5–7 hours until the process of oxidation is complete.

Into a hot suspension with stirring an aqueous suspension containing 13.8 g of $Fe_2O_3$ is added.

The obtained mass is dried at a temperature of about 100° C for 3 hours and then calcined in air at a temperature of 700° C for 4 hours.

The obtained product can be used as iron-antimony catalyst. The yield is 100 per cent of theory. The iron-antimony powder has a specific area of 72 sq.m/g. The attrition strength of the material was determined for particles sizing 100–200 microns in a chamber with an impeller rotating at 3500 rpm for 40 minutes. The yield of fraction +100 micron after the attrition test, which characterized the strength of the material, is 91 per cent.

EXAMPLE 2

A reaction vessel is loaded with 100 ml of water and, with stirring, is added 50 g of antimony trioxide. The mixture is heated to 90° C and about 50 ml of a 30 per cent solution of hydrogen peroxide is added. The mixture is kept at this temperature for 1 hour and then, by small portions, is added 100 ml of a solution of $Fe(NO_3)_3$ (containing 13.8 g of $Fe_2O_3$). The obtained mixture is dried at a temperature of 120°–130° C for four hours and calcined in air at a temperatures of 700° C for 4 hours.

The obtained product has the following composition: 80 per cent of $Sb_2O_5$ and 20 per cent of $Fe_2O_3$. It can be used as a catalyst in the process of oxidation of propylene into acrylonitrile. The end product has the specific surface of 47.6 sq.m/g, its mechanical strength, for the fraction sizing 100–200 micron, as tested in the chamber with a rotating impeller (3500 rpm) for 40 minutes, is 90 per cent.

The capacity of the catalyst with respect to acrylonitrile is 80.3 per cent, the selectivity 57.9 per cent. The capacity of the catalyst was determined on a pass-through-circulatory plant with a boiling fluidized catalyst bed.

EXAMPLE 3

50 g of $Sb_2O_3$ and 41.8 g of $SnSO_4$ are mixed in 300 ml of water and the obtained suspension is heated to 90° C. Into the hot suspension added are 60 ml of a 30 per cent solution of hydrogen peroxide and the components are mixed at a temperature of 90° C until the oxidation process is complete (30–60 minutes). The obtained suspension is dried in a spray drier or a drying cabinet at a temperature of 120°–140° C for 4 hours, then calcined in air at a temperature of 700° C for 3 or 5 hours.

The obtained product contains 70.6 per cent of $Sb_2O_5$ and 29.4 per cent of $SnO_2$, and can be used as a catalyst for oxidation of organic substances.

EXAMPLE 4

132.5 g of $SnSO_4$ and 6.3 g of $Sb_2O_5$ are mixed with 500 ml of water to prepare an aqueous suspension containing 93 per cent of $SnO_2$ and 7 per cent of $Sb_2O_5$. The suspension is oxidized by 100 ml of a 30 per cent solution of hydrogen peroxide at a temperature of 40° C and mixed for 30 minutes. The suspension is then heated to 95° C and kept at this temperature for 30 minutes.

The obtained suspension is dried at a temperature of 120°–150° C and then calcined at a temperature of 700° C for 4 hours. The obtained product can be used as a material for resistors.

EXAMPLE 5

50 g of $Sb_2O_3$ are mixed with 100 ml of water and the obtained suspension is heated to 90° C. Then 75 ml of a 30 per cent solution of hydrogen peroxide are added and the components are mixed for 1 hour at a temperature of 90° C.

Into a thickened suspension, with stirring, is added 75 ml of $Mn(NO_3)_2$ solution containing 12.1 g of MnO. The obtained mixture is dried at a temperature of about 120° C for 4 hours and calcined in air at a temperature of 300° C for 2 hours. The obtained product contains 82 per cent of $Sb_2O_5$ and 18 per cent of MnO, and can be used as a catalyst for oxidation of organic substances.

EXAMPLE 6

50 g of antimony trioxide are mixed with 100 ml of water and the obtained suspension is heated to 95° C. Into the hot suspension added are 40 ml of a 30 per cent solution of hydrogen peroxide and the components are mixed for 30–60 minutes. To the obtained suspension is added 23.5 g of barium hydroxide (as Ba) and at the same temperature the suspension is mixed for 1 hour. The obtained mass is dried for 3 hours and calcined at a temperature of 500° C for 3 hours.

The obtained single-phase product consists of barium antimonate $BaSb_2O_6$. The parameters of the unit cell ($a = 4.63$ A, $c = 9.21$ A) are determined by x-ray structural analysis and correspond to the individual compound.

EXAMPLE 7

The reaction vessel is loaded with 100 ml of water into which, with stirring, is added 50 g of antimony trioxide and the mixture is heated to a temperature of 95° C. Into the hot suspension added are 17–18 ml of a 33 per cent solution of hydrogen peroxide and the mixture is kept at this temperature for a few hours. The obtained mass is aged at room temperature until yellow colour develops.

The obtained material is semi-crystalline antimony tetraoxide $Sb_2O_3 \cdot Sb_2O_5$.

After calcining for 3 hours at a temperature of 470° C the product converts into a crystalline substance and has the orthorhombic unit cell having the following parameters: $a = 4.804$ A, $b = 5.42$ A and $c = 11.78$ A.

EXAMPLES 8, 9, 10, 11, 13, 14, 17, 18

Oxygen compounds or solid solutions of antimony with metals are prepared in conditions similar to those described in Example 2. The specifications of the obtained materials given in the appended Table, are based on the X-ray structural and phase analysis.

EXAMPLES 12, 15 and 16

The oxygen compounds or solid solution of antimony with metals are prepared in conditions similar to those described in Example 3. Their specifications are summarized in the Table.

Table

| Ex. No. | Starting metal compound | Structural formula of oxycompound of antimony with metal | Structure (unit cell) type | Unit cell parameters, A |
|---|---|---|---|---|
| 9 | $AgNO_3$ | $AgSbO_3$ | Ilmenite | 10.23 |
| 10 | $Ba(OH)_2$ | $BaSb_2O_6$ | Trigonal | $a = 5.29$ $c = 5.74$ |
| 11 | $Ca(OH)_2$ | $CaSb_2O_6$ | Tetragonal Rutile | $a = 5.23$ $c = 5.02$ |
| 12 | $Mg(OH)_2$ | $MgSb_2O_6$ | Rutile | $a = 4.63$ $c = 9.21$ |
| 13 | $Al(OH)_3$ | $AlSbO_4$ | Rutile | — |
| 14 | $Cr(NO_3)_3$ | $CrSbO_4$ | Rutile | — |
| 15 | $Pb(NO_3)_2$ | $Pb_3Sb_2O_7$ | Ilmenite | 10.38 |
| 16 | $La_2O_3$ | $Al_{0.5}Sb_{1.5}O_6$ | Tetragonal | $a = 5.15$ $c = 5.17$ |
| 17 | $La_2O_3$ $SnO_2$ | $LaSnSbO_6$ | Tetragonal Tetragonal | $a = 5.30$ $c = 5.18$ |
| 18 | $Co(NO_3)_2$ | $CoSb_2O_6$ | Tetragonal | $a = 4.64$ $c = 9.25$ |
| 19 | $Ni(NO_3)_2$ | $NiSb_2O_6$ | Tetragonal | $a = 4.63$ $c = 9.18$ |

What we claim is:

1. A method for preparing oxygen compounds of antimony comprising in combination (a) oxidizing antimony trioxide with hydrogen peroxide in a quantity not less than stoichiometric in an aqueous medium at a temperature of from 40° to 100° C to form a suspension of hydrated antimony pentoxide, (b) maintaining said suspension of hydrated pentoxide at said temperature, (c) reacting said suspension with at least one of the salt, hydroxide or oxide of an element selected from the group consisting of group Ce, Te, P, B and metallic elements of IB, IIA, IIB, IIIA, IIIB, IVA, IVB, VA, VB, VIB, VIIB and VIII of the Periodic Table, (d) drying and then (e) calcining the resulting material to form the desired compound.

2. A method according to claim 1 in which the salt, hydroxide or oxide is selected from the group consisting of Fe, Sn, Bi, Ni, Co, V, Mo, W, Cr, Ce, Mn, Ti, Al, $Sb^{III}$, Cu, Ca, Ba, Mg, Pb, Nb, Ta, Te, P and B, the drying temperature is from 100° to 250° C and the calcining temperature is from 300° to 700° C.

3. A method according to claim 1 in which iron hydroxide is the hydroxide, the weight ratio of the iron hydroxide to antimony pentoxide being 1:4.

4. A method according to claim 1 wherein the oxidation temperature is about 80° C.

* * * * *